United States Patent [19]

Margel et al.

[11] Patent Number: 4,783,336
[45] Date of Patent: * Nov. 8, 1988

[54] POLYACROLEIN-TYPE MICROSPHERES

[75] Inventors: Shlomo Margel; Uzi Beitler, both of Rehovot, Israel

[73] Assignee: Yeda Research and Development Company, Ltd., Rehovot, Israel

[*] Notice: The portion of the term of this patent subsequent to Nov. 12, 2002 has been disclaimed.

[21] Appl. No.: 772,387

[22] Filed: Sep. 4, 1985

Related U.S. Application Data

[63] Continuation-in-part of Ser. No. 330,451, Dec. 14, 1981, Pat. No. 4,552,812.

[30] Foreign Application Priority Data

Jul. 1, 1981 [IL] Israel ......................................... 63220

[51] Int. Cl.⁴ .......................... A61K 9/58; B01J 13/02; C08F 16/34; C12N 11/08
[52] U.S. Cl. ................................. 424/462; 260/513 B; 424/94.3; 424/497; 427/213.34; 428/402.24; 428/407; 436/501; 436/532; 436/547; 523/223; 524/547; 526/315; 526/909
[58] Field of Search ............. 427/213.34; 428/402.24, 428/407; 424/33, 462, 497; 523/223; 524/457; 526/315, 909

[56] References Cited

U.S. PATENT DOCUMENTS

| | | | |
|---|---|---|---|
| 3,824,114 | 7/1974 | Vassiliades et al. | 264/4.7 X |
| 4,003,846 | 1/1977 | Kuhn et al. | 427/213.34 |
| 4,046,720 | 9/1977 | Rembaum et al. | 526/312 X |
| 4,157,323 | 6/1979 | Yen et al. | 424/33 X |
| 4,267,235 | 5/1981 | Rembaum et al. | 428/407 |
| 4,269,821 | 5/1981 | Kreuter et al. | 424/33 X |
| 4,413,070 | 11/1983 | Rembaum | 523/223 |
| 4,552,812 | 11/1985 | Margel et al. | 428/402.24 X |
| 8,183,217 | 5/1965 | Serniuk et al. | 526/315 X |

OTHER PUBLICATIONS

Margel et al.: "Polyacrolein Microspheres as a New Tool in Cell Biology", J. Cell Science, vol. 56, pp. 157-175 (1982).
Kronick et al.: "Magnetic Microspheres Prepared by Redox Polymerization" ..., Science, vol. 200, Jun. 2, 1978, pp. 1074-1076.
Ryder, Jr. et al., "Polymerization of Acrolein by Redox Initiation", Journal of Polymer Science: Part A, vol. 3, pp. 3459-3469 (1965).
Pourfarzaneh et al.: "Composite Polyacrolein-Coated Cellulose Magnetizable Particles ..." Clinica Chimica Acta 111: 61-63 (Mar. 1981).

Primary Examiner—Richard D. Lovering
Attorney, Agent, or Firm—John P. White

[57] ABSTRACT

Suspension polymerization of acrolein type compounds in the presence of appropriate surfactants results in the formation of microspheres in size ranging from 0.03 to 80 microns. Fluorescent and magnetic microspheres are obtained by carrying out the same polymerization in the presence of appropriate fluorochromic or ferrofluidic compounds, respectively. Hybrido-polyacrolein microspheres are obtained by grafting one type of such microspheres on another type. Immunomicrospheres were formed by binding covalently at physiological pH appropriate proteins to the microspheres. The immunomicrospheres can be used for various biological applications, such as specific markers for labeling cell surface receptors, for cell separation, for diagnostic purposes, etc.

13 Claims, 7 Drawing Sheets

POLYACROLEIN-TYPE MICROSPHERES

BACKGROUND OF THE INVENTION

This application is a continuation-in-part of U.S. Ser. No. 330,451 filed Dec. 14, 1981, now U.S. Pat. No. 4,552,812, issued Nov. 12, 1985, the contents of which are hereby incorporated by reference into the present application.

This invention relates to microspheres produced from acrolein type compounds. The microspheres may be fluorescent or magnetic and hybridomicrospheres having multiple characteristics may be prepared. The microspheres are useful for various purposes such as cell labeling, cell separation, receptor separation, affinity chromatography, diagnostic purposes, enzyme immobilization, drug delivery, etc. The microspheres can be bound to various compounds having amino groups, such as drugs, enzymes, antibodies and antigens which retain their activity. The novel acrolein-type compound microspheres can be prepared by a variety of processes which are adjusted according to the desired product with regard to diameter and other properties.

There exists a great interest in the scientific community in developing a reliable technique for the isolation of cell surface receptors and for separating cells of various types. Labeling of specific receptors on cell surfaces has great importance for understanding various biological phenomena, such as cell-cell recognition in development, cell communication and differences between normal and tumor cell surfaces. Mapping of antigens and carbohydrate residues on the surface of cells has been studies intensively by various techniques, for example, using fluorescent (or radioactive) antibodies or lectins, or by binding biological macromolecules such as ferritin, hemocyanin, viruses and peroxidase to antibodies or lectins. The biological macromolecules were used as markers for transmission electron microscopy (TEM). Polymeric microspheres were also used as markers for cell labeling. Polystyrene latex particles have been utilized as immunological markers for use in the TEM techniques. Such particles, because of their hydrophobic character, stick non-specifically to many surfaces and molecules and therefore limit their broad application. Many other types of polymeric microspheres which were hydrophilic were synthesized and were used for labeling cell surface receptors (Table 1).

TABLE 1

| Classes of Hydrophilic Crosslinked Microspheres | |
|---|---|
| 1. Em classes: | methylmethacrylate (MMA), 2-hydroxyethylmethacrylate (HEMA), methacrylic acid (MA), and ethylene glycol dimethacrylate (EGDMA).[a] |
| 2. L class: | HEMA, MA, and bisacrylamide (BAM).[b] |
| 3. BAH class: | HEMA, acrylamide (AA), MA, and BAM.[b] |
| 4. DMA class: | HEMA, 2-dimethylaminoethylmethacrylate (DMA), and BAM.[b] |
| 5. PVP class: | 4-vinyl pryridine alone or with HEMA and/or AA.[b] |

[a] Emulsion polymerization
[b] Cobalt gamma radiation

Figure 1:
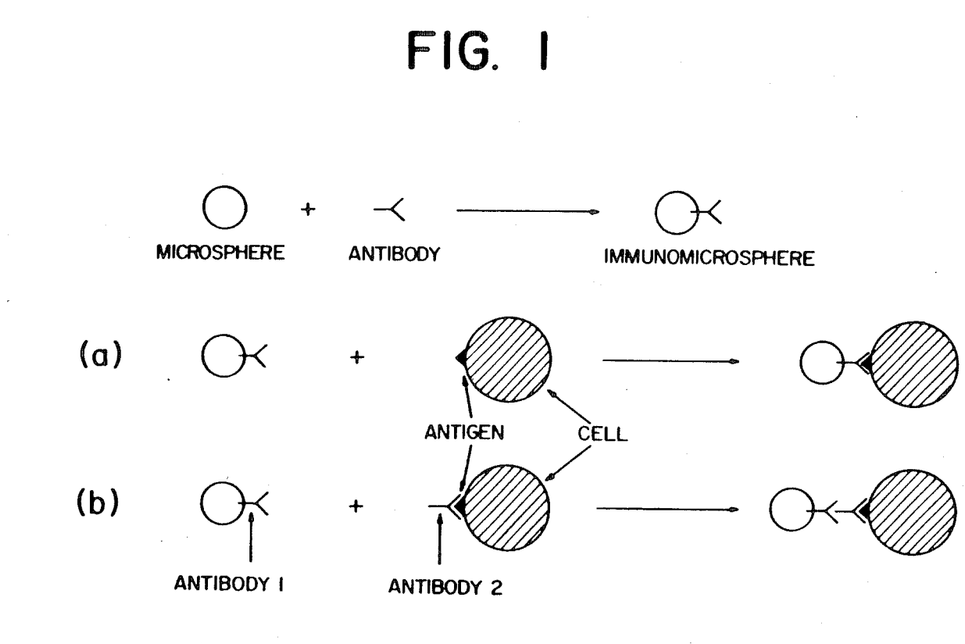
FIG. 1 is a schematic representation of (a) direct and (b) indirect labeling of living cells by means of immunomicrospheres.

The labeling procedure was carried out by using either the direct or the indirect method (FIG. 1).

In both methods the first step requires the covalent binding of a purified antibody to a microsphere through the functional groups on its surface. In the direct method the immunomicrospheres (microspheres to which a specific antibody is covalently bound) seek out the cell antigens and bind to it, and in the indirect method an intermediate antibody is employed.

Figure 2:
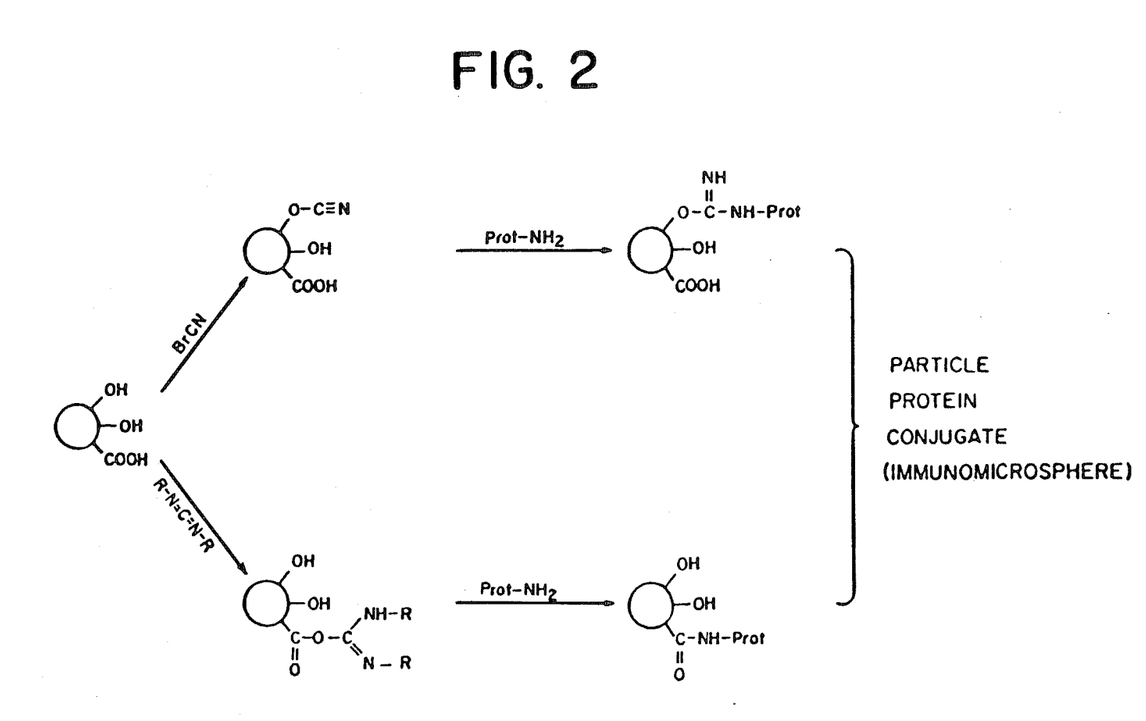
FIG. 2 is a reaction scheme for the cyanogen bromide and the carbodiimide procedures.
Figure 3:
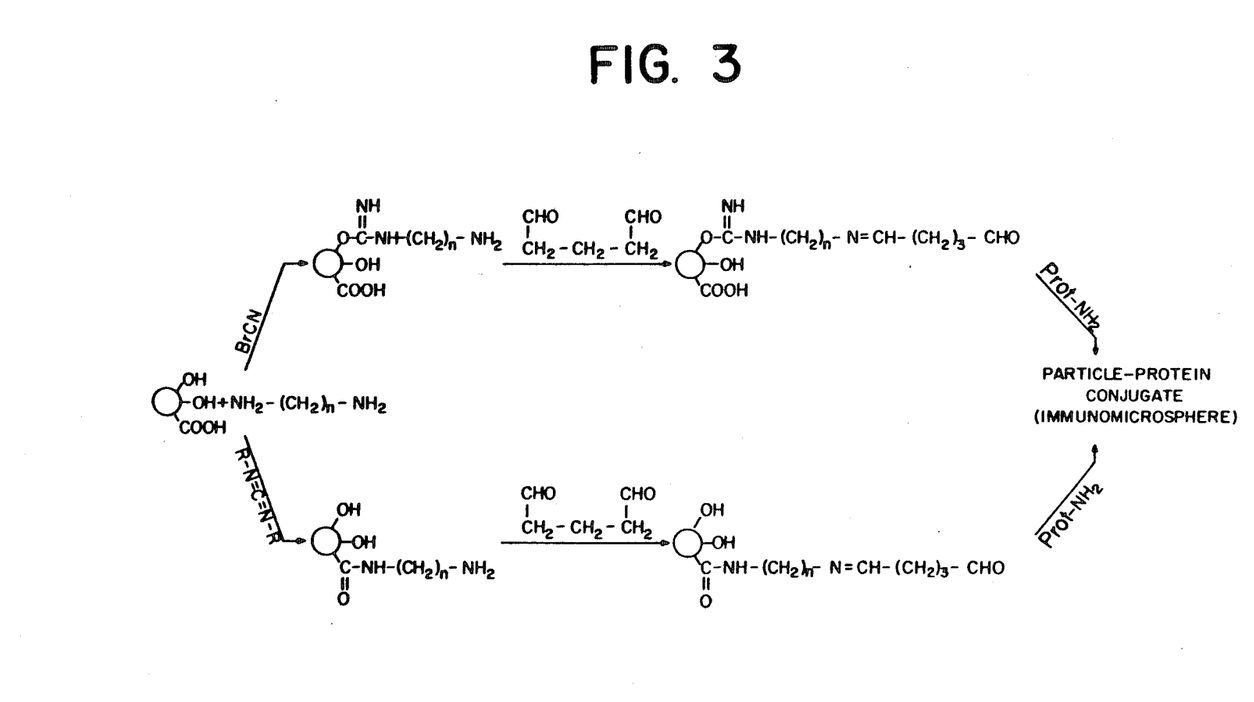
FIG. 3 is a reaction scheme for the glutaraldehyde procedure.

The microspheres, depending on the initial monomer composition, had either carboxyl, hydroxyl, amide and/or pyridine groups on their surface. The functional groups were used to covalently bind antibodies and other proteins to the microspheres by using either the cyanogen bromide, carbodiimide, or glutaraldehyde methods (FIGS. 2 and 3).

The last step of the microspheres derivatization technique, prior to protein binding, consisted of a reaction with glutaraldehyde, designed to introduce reactive aldehyde groups on the surface of the beads.

Recently, a patent was filed by A. Rembaum and S. Margel describing a method for preparation of polyglutaraldehyde microspheres - U.S. Ser. No. 21,988, filed Mar. 19, 1979, now U.S. Pat. No. 4,267,235, issued May 12, 1981. These polyaldehyde microspheres were used for binding in a single step appropriate proteins at physiological pH.

SUMMARY OF THE INVENTION

The present invention relates to novel polyacrolein microspheres, homo- and hybrido-microspheres and to their biological potential uses.

Polyacrolein Microspheres

Polyacrolein microspheres were prepared in two ways:

(a) polymerization of acrolein under basic conditions in the presence of appropriate surfactants - anionic microspheres;

(b) radical polymerization of acrolein in the presence of appropriate surfactants, without or in presence of other acrylic monomers - radical microspheres.

(a) Basic Conditions

Figure 4:
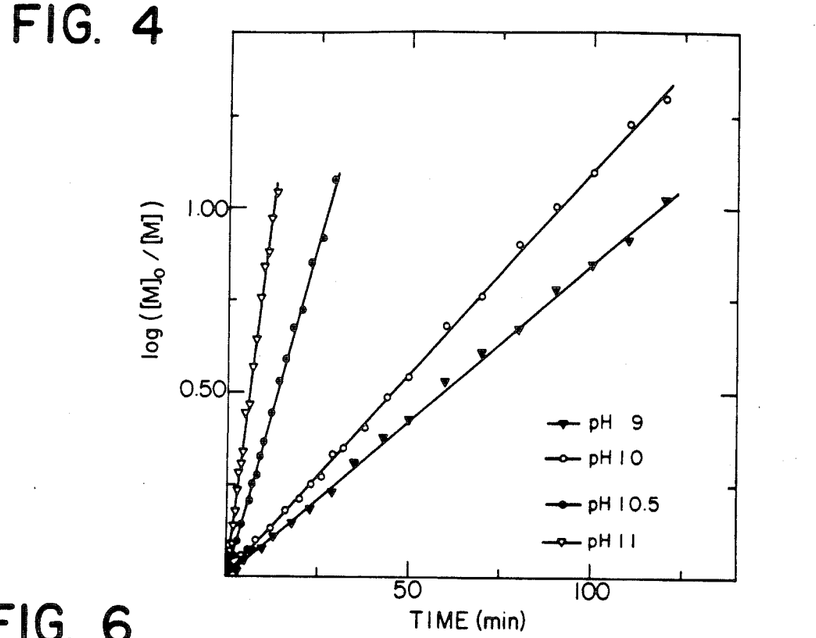
FIG. 4 illustrates first-order rate plates, at various pH's, for acrolein polymerization in aqueous media (temp. 23° C., acrolein concentration 2%)
Figure 5A:
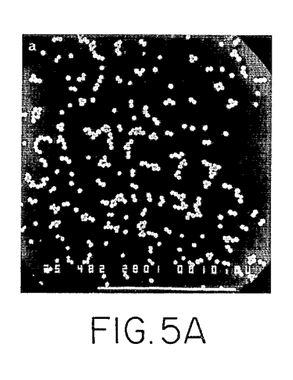
FIG. 5 illustrates scanning electron microscopy photomicrographs of polyacrolein microspheres of various sizes.
Figure 5B:
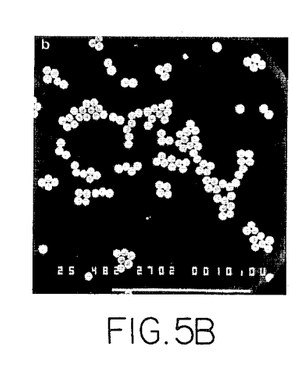
Figure 5C:
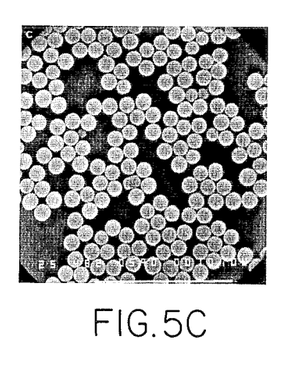
Figure 5D:
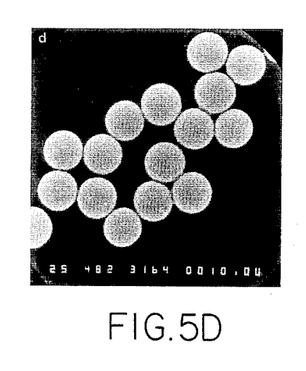
Figure 5E:
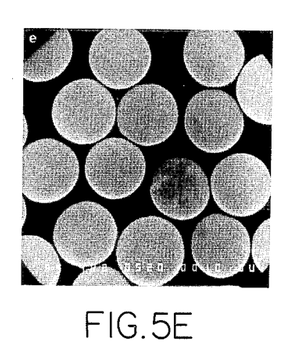
Figure 5F:
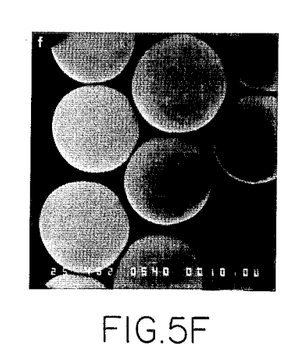

Polymerization of acrolein, in aqueous media under basic conditions, results in the formation of the water insoluble polyacrolein polymer. The polymerization is first order related to acrolein concentration and the rate is dependent on the pH of the polymerization (FIG. 4) - the higher the pH, the faster the polymerization. Analysis by IR spectroscopy confirms the presence of aldehyde groups as well as hydroxyl groups, carboxyl groups, ether groups and double bonds. At very high pH (higher than 13.5), due to Cannizzaro reaction, (two aldehyde groups react to give one hydroxyl group and one carboxyl group) a water soluble polyacrolein is obtained.

(b) Radical Polymerization of Acrolein

Polymerization of acrolein in aqueous media was carried out by using redox initiators, such as ammonium persulfate-silver nitrate, or using redox initiators, such as ammonium persulfate-silver nitrate, or cobalt radiation (Co). The structure of the polyacrolein in a simplified form is where n is an integer of 100 to 10,000, and it is different from that obtained by the basic polymerization. The hydrophilicity (and therefore the specificity towards cells) of the polyacrolein, obtained by the radical polymerization, can be increased by either stirring the polymer at a high pH (approximately pH 12) of an aqueous solution (due to Cannizzaro reaction) or by copolymerizing acrolein with hydrophilic monomers (such as hydroxy methyl-methacrylate).

Anionic Polyacrolein Microspheres

Figure 6:
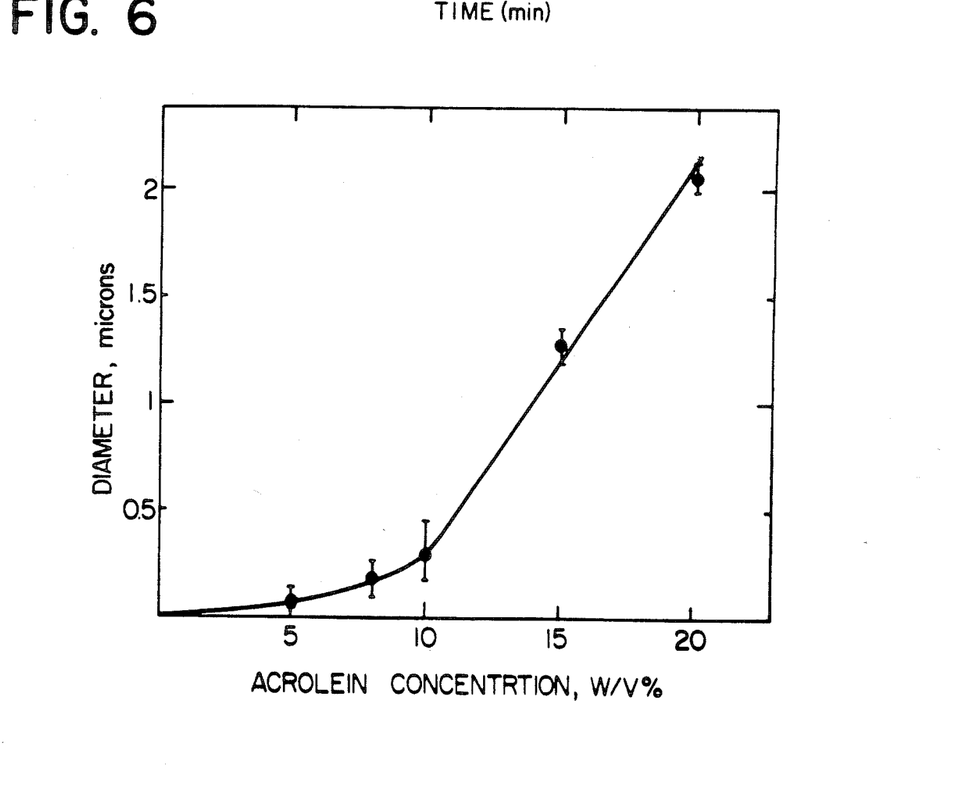
FIG. 6 illustrates size of polyacrolein microspheres as a function of acrolein concentration (temp. 23° C., pH 10, surfactant (PGL-NaHSO$_3$) 0.5% w/v)
Figure 7:
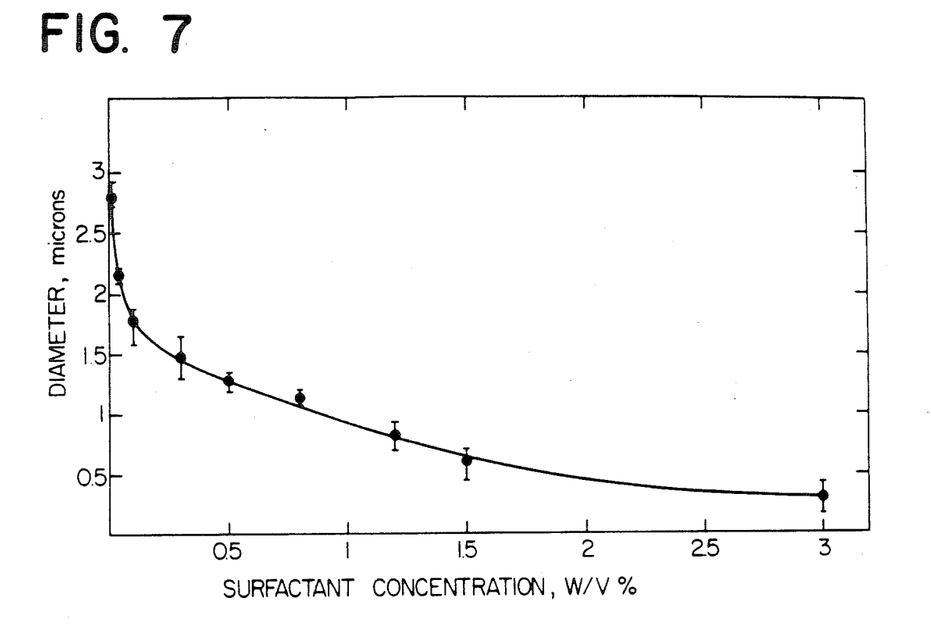
FIG. 7 illustrates size of polyacrolein microspheres as a function of surfactant (PGL-NaHSO$_3$) concentration (temp. 23° C., pH 10, acrolein 15% w/v)
Figure 8:
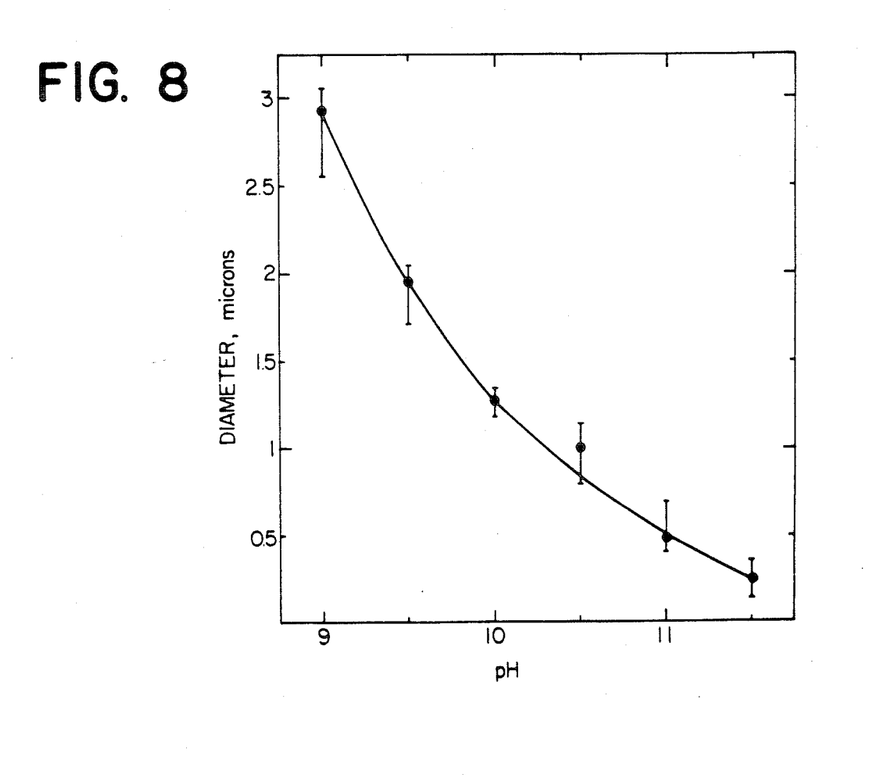
FIG. 8 illustrates size of polyacrolein microspheres as a function of pH polymerization (temp. 23° C., acrolein 15% w/v, surfactant (PGL-NaHSO$_3$) 0.5% w/v.

Polymerization of acrolein, in aqueous media under basic conditions and in the presence of appropriate surfactants (ionic, i.e. anionic and cationic), results in the formation of the polyacrolein microspheres (FIG. 5). The size of the microspheres can be controlled by changing the acrolein concentration (FIG. 6), surfactant concentration (FIG. 7) or pH of the polymerization (FIG. 8). Addition of dimethylformamide to the aqueous medium (or other correlated solvents e.g. dimethylsulfoxide) increases the solubility of acrolein and results in the formation of uniform large polyacrolein beads.

Fluorescent or magnetic microspheres were obtained by carrying out the acrolein polymerization in the presence of appropriate fluorochromic (e.g. fluorescein isothiocyanate, aminofluorescein, tetramethyl rhodamine isothiocyanate, etc.) or ferrofluidic compounds, respectively.

Radical Polyacrolein Microspheres

Radical polymerization of acrolein, in the presence of appropriate surfactants, results in the formation of the radical microspheres (which have a different structure than that obtained by the basic polymerization.) Increasing the pH (of the suspension solution) to a value between 11.5 to 13 will increase the hydrophilicity of these microspheres. Copolymerization of acrolein with hydrophilic monomers, in the presence of appropriate surfactants, also produces more hydrophilic microspheres.

Hybrido-Microspheres

Figure 9A:
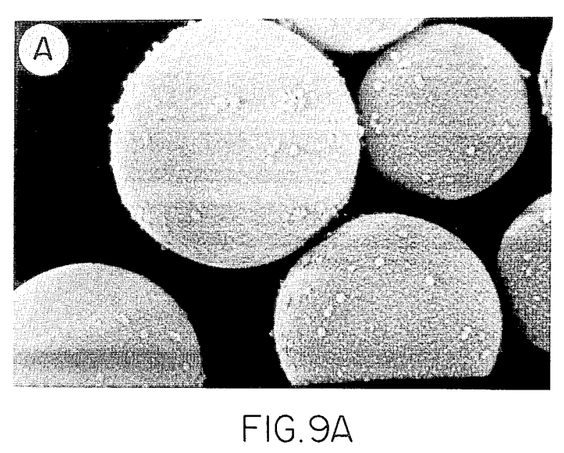
FIG. 9A illustrates 2.0 micron average anionic polyacrolein microspheres coated with 0.1 micron radical polyacrolein microspheres ($\times$4600)
Figure 9B:
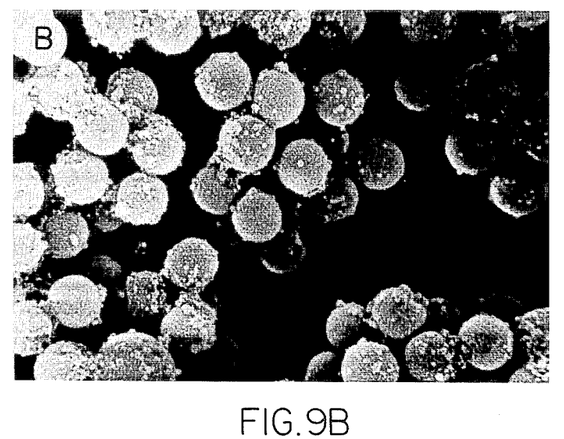
FIG. 9B illustrates 2.0 micron anionic polyacrolein microspheres coated with 0.1 radical polyacrolein microspheres ($\times$12000).

The anionic polyacrolein microspheres have been coated with the radial microspheres (FIG. 9). The relatively large anionic microspheres are completely covered with the smaller radical beads, e.g. 2.0 micron anionic beads are covered with 0.1 micron radical beads. However, increasing the size of the radical microspheres to 0.5 microns will cause the radical beads to detach from the surface of the anionic microspheres. The coating procedure is based on the radical polymerization of acrolein in the presence of the anionic microspheres. The mechanism of the coating involves the grafting of the radical microspheres onto the surface of the anionic beads through their double bonds.

Based on this grafting technique the anionic polyacrolein microspheres had been coated with many other types of polymeric microspheres, e.g. polyvinylpyridine microspheres (0.1 micron diameter) were grafted on the surface of the anionic polyacrolein beads (2 micron diameter) by carrying out the radical polymerization of 4-vinylpyridine in the presence of the anionic polyacrolein beads.

BRIEF DESCRIPTION OF DRAWINGS

The invention is illustrated with reference to the enclosed Figures in which:

FIG. 9 illustrates scanning electron microscopy photomicrographs of hybrido polyacrolein microspheres;

EXAMPLE 1

Synthesis of the Surfactant PGL-NaHSO$_3$:

This surfactant was prepared by the reaction of polyglutaraldehyde (PGL) and sodium hydrogen sulfite (NaHSO$_3$), as follows: 12.5 g NaHSO$_3$ were dissolved in 30 ml H$_2$O. 5 g of PGL was then added and the solution was stirred until all the PGL was dissolved. The solution was dialyzed extensively against H$_2$O (molecular weight cutoff of the dialyzing bag was 3,500), and then lyophilized.

EXAMPLE 2

Formation of Polyacrolein Microspheres under Basic Conditions:

Aqueous NaOH solution (0.2N) was added dropwise to a solution containing 8% w/v acrolein and 0.55 of the surfactant PGL-NaHSO$_3$ until pH 10.5 was reached. The reaction was continued for 2 hours, and the produced microspheres (diameter 0.1 microns) were then washed four times by centrifugation at 2000$\times$g for 20 minutes. By varying the surfactant and/or acrolein concentration, the pH of polymerization or the solvent, the size of the microspheres can be changed in a predictable way.

EXAMPLE 3

Magnetic Microspheres

Example 2 was repeated in the presence of a 5% (v/v) of ferrofluidic solution (aqueous dispersion of Fe$_3$O$_4$, sold by Ferrofluidics, Burlington, Mass., No. A01 5% w/v) and resulted in the formation of magnetic polyacrolein microspheres of average size of 0.04 microns. The magnetic microspheres were washed by dialysis and then separated from diamagnetic impurities by means of a permanent magnet.

EXAMPLE 4

Fluorescent Microspheres

Example 2 was repeated in the presence of 0.008% (w/v) tetramethyl rhodamine isothiocyanate and resulted in the formation of 0.1 micron diameter fluorescent polyacrolein microspheres.

EXAMPLE 5

Example 2 was repeated in the presence of methacrolein (instead of acrolein). Microspheres with average size of 0.1 microns were produced.

EXAMPLE 6

Example 2 was repeated in the presence of crotonaldehyde (instead of acrolein). Microspheres with average size of 0.2 microns were obtained.

EXAMPLE 7

The procedure of Example 2 was repeated substituting the surfactant PGL-NaHSO$_3$ by the anionic surfactants Dowfax 2A1 (or Dowfax 3B2). Polyacrolein microspheres having average size of 0.1 microns were obtained.

EXAMPLE 8

The procedure of Example 2 was repeated substituting the surfactant PGL-NaHSO$_3$ with the non-ionic surfactant Polysurf 10-36B (based on a copolymer of acrylamide and isobutoxy acrylamide, provided by Bartig Industries, Inc., Birchwood Ave., New Canaan, Conn. 06840 USA). No polyacrolein microspheres were obtained by this process.

EXAMPLE 9

Aqueous NaOH (0.2N) was added in a dropwise fashion to an aqueous solution containing 10% dimethyl formamide 25% (w/v) acrolein and 0.08% (w/v) of the surfactant PGL-NaHSO$_3$ until pH 11.5 was reached. The reaction was continued for an hour and then the produced monodispersed microspheres (3 micron diameter) were washed 4 times by spinning at 500×g for 10 minutes.

EXAMPLE 10

Aqueous NaOH solution (0.2N) was added to a stirred solution at 200 rpm containing 3.6% (v/v) dimethyl formamide, 25% (v/v) acrolein and 0.04% (w/v) of the surfactant PGL-NaHSO$_3$ until pH 11.0 was reached. The reaction was continued for an hour and then the produced microspheres were washed several times by centrifugation. Scanning Electron Microscopy showed the formation of extremely uniform microspheres of 5.5 micron diameter.

EXAMPLE 11

Ten ml of an aqueous solution containing 10% (w/v) dimethyl formamide and 0.3% (w/v) of the surfactant PGL-NaHSO$_3$ was brought to pH 11.2. The solution was stirred gently and 5 ml of acrolein was added. The reaction continued for 15 minutes and the produced beads (average size of 80 microns) were washed several times by decantation.

EXAMPLE 12

Formation of Polyacrolein Microspheres under Radical Conditions

One Hundred ml of an aqueous solution containing 9% (w/v) acrolein and 0.5% (w/v) polyethylene oxide (m.w. 100,000) was deaerated with argon and radiated then with cobalt source (1 Mega rad). The produced microspheres (0.15 micron size) were washed by centrifugation 4 times at 2000×g for 30 minutes.

EXAMPLE 13

Example 12 was repeated in the presence of 5% (w/v) of hydroxymethyl methacrylate. Microspheres in average size of 0.2 microns were obtained.

EXAMPLE 14

Example 12 was repeated in the presence of 1% (w/v) N,N'-methylene-bis-(acrylamide) as crosslinker. Microspheres having average size of 0.15 microns were obtained.

EXAMPLE 15

Example 12 was repeated in the presence of methacrolein. Microspheres in average size of 0.2 microns were obtained.

EXAMPLE 16

Example 15 was repeated in the presence of 0.008% (w/v) of fluorescein isothiocyanate and resulted in the formation of 0.2 microns fluorescent polymethacrolein microspheres.

EXAMPLE 17

Example 12 was repeated in the presence of methyl vinyl ketone. Microspheres in average size of 0.2 microns were obtained.

EXAMPLE 18

The microspheres prepared as in Example 12 were treated for 12 hours in a basic aqueous solution (pH 12.0) and then washed four times by spinning at 2000×g for 30 minutes. The hydrophilic microspheres obtained had an average size of 0.15 microns.

EXAMPLE 19

One hundred twenty ml of an aqueous solution containing 9% (w/v) acrolein, 0.5% (w/v) polyethylene oxide (m.w 100,000) and 1.0 mmol of ammonium persulfate was deaerated with argon. 1.0 mmol of AgNO$_3$ was then added to the stirred solution. The reaction continued for 12 hours and the produced beads with average size of 0.1 microns were washed 4 times by spinning at 2000×g for 20 minutes.

EXAMPLE 20

Example 19 was repeated in the presence of 5% (v/v) of ferrofluidic solution and resulted in the formation of magnetic polyacrolein microspheres of average size of 0.05 microns. The magnetic microspheres were washed by dialysis and then separated from diamagnetic impurities by means of a permanent magnet.

EXAMPLE 21

Four ml of an aqueous solution containing 9% (w/v) acrolein, 0.5% (w/v) polyethylene oxide (m.w. 100,000) and 100 mg of the anionic polyacrolein beads of 2.0 microns size was deaerated with argon. The stirred solution was then radiated with cobalt source (1 mega rad). The grafted microspheres (FIG. 9) were washed from excess of 0.1 micron radical microspheres by spinning four times at 500×g for 10 minutes.

EXAMPLE 22

Four ml of an aqueous solution containing 8% (w/v) acrolein, 0.5% (w/v) polyethylene oxide (m.w.

100,000), 0.06 mmol of ammonium persulfate and 100 mg of the anionic polyacrolein beads of 2.0 micron size was deaerated with argon to the stirred solution 0.06 millimole of $AgNO_3$ was then added. The reaction continued for 12 hours and the grafted microspheres were washed by centrifugation 4 times at 500×g for 10 minutes.

EXAMPLE 23

The procedure of Example 20 was repeated substituting acrolein with 1% (w/v) 4-vinyl pyridine.

EXAMPLE 24

The procedure of Example 21 was repeated substituting acrolein with 1% (w/v) 4- vinyl pyridine.

EXAMPLE 25

Characterization of the Microspheres

Polyacrolein microspheres obtained by basic radical irradiation, and radical redox polymerization were tested for aldehyde group, double-bond, and carboxyl group content. Additionally, the intrinsic viscosities of 0.1 microgram microspheres were measured in aqueous solutions of sodium bisulfite containing a weight ratio of 3/1 between the sodium bisulfite and the microspheres. The intrinsic viscosity of the PGL microspheres was measured in DMF. The properties were found to vary significantly among the microsphere types, distinguishing them from each other. Table 2 presents aldehyde groups, double-bond, carboxyl group content, and intrinsic viscosities of basic, radical irradiated, and radical redox microspheres.

TABLE II

Aldehyde, Double-Bond, Carboxyl Content and Intrinsic Viscosities of the Polyaldehyde Microspheres[a]

| Microspheres | Aldehyde content (mmol/g microspheres) | Double-bond content (mmol/g microspheres) | Carboxyl content (mmol/g microspheres) | Intrinsic viscosities of 0.1 micron microspheres (dL/g) |
|---|---|---|---|---|
| PGL | 4.9 | 3.5 | 0.3 | 0.1 |
| "Alkaline" PA | 2.9 | 10.9 | 0.34 | 0.05 |
| "Irradiated" PA | 9.3 | 2.0 | —[a] | 0.16 |
| "Redox" PA | 12.0 | 1.6 | —[a] | 0.51 |

[a]The carboxyl content is too low for precise measurement.

EXAMPLE 26

Sodium bisulfite 150 mg was added to three separate solutions containing 100 mg (in 2 ml $H_2O$) of radical irradiated microspheres (obtained by 2 Mrad Cobalt irradiation), radical redox microspheres, and basic microspheres respectively. The solutions were shaken for 12 hours. The bisulfite adduct of the basic and radical redox microspheres became water soluble, while that of the radical irradiated microspheres did not dissolve in water.

EXAMPLE 27

Labeling of Red Blood Cells with Microspheres

Polyacrolein microspheres obtained by basic polymerization were shaken for 2 hours, at 4° C., with purified goat-anti-rabbit IgG (GxRIgG) (1 mg microspheres, 0.1 mg GxRIgG in total volume of 0.15 ml PBS). Thereafter unbound antibody was separated by passing the microsphere suspension through a Sepharose 4B column. The separating was monitored spectrophotometrically at A=280 nm. The free aldehyde groups of the conjugate microspheres antibody were quenched with 2% (w/v) bovine serum albumin solution for several hours at 4° C.

Fresh human RBC, from a normal donor, were shaken for 50 min at 4° C., with rabbit anti human RBC (*Cappel Lab. Inc.) ($10^6$ human RBC with rabbit against human RBC in 0.1 ml PBS solution). The sensitized cells were separated and washed 4 times by spinning the cell suspension in an international centrifuge at 500×g. The goat-anti-rabbit derivatized microspheres were then added to the sensitized human RBC and the mixture was shaken at 4° C. for 1 hour. The RBC were separated from unreacted derivatized microspheres by centrifugation 3 times at 500×g. The labeled cells were resuspended in PBS and were examined by light fluorescent microscopy and with fluorescence-activated cell sorter (FACS-11) (Becton-Dickinson - photomultiplier 600V, 2 filters - 550 nm).

EXAMPLE 28

Separation of Turkey RBC from Human RBC

A mixture containing $10^6$ human RBC and $10^6$ turkey RBC was treated with magnetic microspheres by using the former labeling procedure. Then a small magnet was fitted on the outside wall of a vial containing PBS solution of the cell mixture. After 10 minutes, cells which were not attracted to the wall were isolated. The attracted cells were resuspended with PBS and the magnetic separation was repeated twice. Examination with light microscopy showed that more than 90% of the attracted cells were human RBC.

Polyacrolein microspheres can be used for cell labeling and cell separation of other systems (e.g. labeling and separation of B and T cells) as well as for other purposes such as drug delivery, enzyme immunoassay, and enzyme mobilization.

What is claimed is:

1. A polyacrolein-type microsphere produced by subjecting an aqueous mixture of a polymerizable acrolein-type monomer to polymerization in the presence of an effective amount of a suitable ionic surfactant which promotes uniform microsphere formation upon polymerization of the monomer so as to form a polyacrolein-type microsphere, the polymerization being effected at a pH between 8.0 and 13.7, and recovering the resulting microsphere and purifying the microsphere so recovered, the microsphere having an aldehyde content of about 2.9 mmol/gram of microspheres, a double-bond content of about 10.9 mmol/gram of microspheres and a carboxyl content of about 0.34 mmol/gram of microspheres.

2. A polyacrolein-type microsphere of claim 1 having a diameter from 0.03 to 80 microns.

3. A polyacrolein microsphere of claim 1, wherein the ionic surfactant is PGL-$NaHSO_3$.

4. A polyacrolein-type microsphere of claim 1, wherein the mixture and resulting microsphere additionally contain a fluorescent dye.

5. A polyacrolein-type microsphere of claim 1, wherein the mixture and resulting microsphere contain ferrofluidic material.

6. A polyacrolein-type microsphere of claim 1 to which a compound containing at least one primary amine group is bound.

7. A polyacrolein-type microsphere of claim 6, wherein the compound is a drug, antibody, antigen, enzyme or other protein.

8. A polyacrolein-type microsphere having a diameter from 0.03 to 80 microns produced by subjecting under an inert atmosphere and suitable conditions an aqueous mixture of a polymerizable acrolein-type monomer to polymerization in the presence of an effective amount of a suitable surfactant which promotes uniform microsphere formation upon polymerization of the monomer, an oxidizing agent and reducing agent, the oxidizing agent and reducing agent both being present in amounts capable of initiating a redox reaction so as to effect polymerization of the acrolein-type monomer and microsphere formation, recovering the resulting microsphere and purifying the microsphere so recovered, the microsphere having an aldehyde content of about 12.0 mmol/gram of microspheres and a double-bond content of about 1.6 mmol/gram of microspheres.

9. A polyacrolein microsphere of claim 8, wherein the monomer is acrolein and the surfactant is polyethylene oxide.

10. A polyacrolein-type microsphere of claim 8, wherein the mixture and the resulting microsphere contain a fluorescent dye.

11. A polyacrolein-type microsphere of claim 8, wherein the mixture and the resulting microsphere contain ferrofluidic material.

12. A polyacrolein-type microsphere of claim 8 to which a compound containing at least one primary amine group is bound.

13. A polyacrolein-type microsphere of claim 12, wherein the compound is a drug, antibody, antigen, enzyme or other protein.

* * * * *